US012329449B2

(12) United States Patent
Mickelsen et al.

(10) Patent No.: US 12,329,449 B2
(45) Date of Patent: Jun. 17, 2025

(54) MULTI-SENSOR PATCH AND SIGNAL ANALYZER THAT ENABLE SAFE CARDIAC ABLATION

(71) Applicant: FIELD MEDICAL, INC., Cardiff By The Sea, CA (US)

(72) Inventors: Steven Mickelsen, Cardiff By The Sea, CA (US); The Quyen Nguyen, San Diego, CA (US); Eduardo Jimenez, Fallbrook, CA (US)

(73) Assignee: FIELD MEDICAL, INC., Dover, DE (US)

( * ) Notice: Subject to any disclaimer, the term of this patent is extended or adjusted under 35 U.S.C. 154(b) by 0 days.

(21) Appl. No.: 18/882,606

(22) Filed: Sep. 11, 2024

(65) Prior Publication Data

US 2025/0082402 A1     Mar. 13, 2025

Related U.S. Application Data

(60) Provisional application No. 63/581,958, filed on Sep. 11, 2023.

(51) Int. Cl.
*A61B 18/16*     (2006.01)
*A61B 18/00*     (2006.01)

(52) U.S. Cl.
CPC .... *A61B 18/16* (2013.01); *A61B 2018/00351* (2013.01); *A61B 2018/00577* (2013.01); *A61B 2018/00839* (2013.01); *A61B 2018/165* (2013.01); *A61B 2018/167* (2013.01)

(58) Field of Classification Search
CPC .......... A61B 18/16; A61B 2018/00351; A61B 2018/00577; A61B 2018/00839; A61B 2018/165; A61B 2018/167
See application file for complete search history.

(56) References Cited

U.S. PATENT DOCUMENTS

| | | | |
|---|---|---|---|
| 2016/0166310 A1* | 6/2016 | Stewart | A61B 18/1492 606/34 |
| 2017/0231490 A1* | 8/2017 | Toth | G16H 40/63 600/558 |
| 2019/0231421 A1* | 8/2019 | Viswanathan | A61N 1/056 |
| 2022/0344025 A1* | 10/2022 | Bort | A61B 5/341 |

* cited by examiner

*Primary Examiner* — Khadijeh A Vahdat
(74) *Attorney, Agent, or Firm* — ARC IP Law, PC; Joseph J. Mayo (57) ABSTRACT

A system that enables safe cardiac pulsed field ablation by using multiple types of sensors on a patch to detect and cross-check that the heartbeat is in a safe phase to receive an ablation pulse. The patch may contain for example any or all of ECG electrodes, PPG sensors, accelerometers, and microphones. The patch may also contain one or more pulse return electrodes for unipolar ablation. A signal analyzer coupled to a pulse generator may receive sensor data from the patch and may analyze this data to determine the heartbeat phase. If data from different sensors are inconsistent, then pulse generation may be disabled as a safety feature. Otherwise, pulses may be enabled when the heartbeat is in a safe phase; for example, pulses may be excluded during the T wave.

13 Claims, 9 Drawing Sheets

MULTI-SENSOR PATCH AND SIGNAL ANALYZER THAT ENABLE SAFE CARDIAC ABLATION

This application claims the benefit of U.S. Provisional Patent Application Ser. No. 63/581,958 filed 11 Sep. 2023, the specification of which is hereby incorporated herein by reference.

BACKGROUND OF THE INVENTION

Field of the Invention

One or more embodiments of the invention are related to the field of medical devices used for tissue ablation. More particularly, but not by way of limitation, one or more embodiments of the invention enable a multi-sensor patch and signal analyzer that enable safe cardiac ablation.

Description of the Related Art

Catheters with attached electrodes are widely used for tissue ablation to address a variety of medical issues. For example, for cardiac applications specialized catheters have been invented to deliver pulsed field ablation (PFA) to treat dysfunctions such atrial fibrillation.

Safe cardiac PFA treatment requires that ablation energy be provided at specific points in the heartbeat cycle. For example, there may be vulnerable periods during the cycle when PFA should not be delivered, such as the T-wave. Existing cardiac ablation systems either do not address this vulnerability, or they use solutions that may compromise patient safety with single points of failure. Furthermore, existing systems that attempt to measure cardiac activity may integrate sensing into the ablation catheters, which inherently limits the complexity of sensor configurations that may be used. There are no known solutions that measure heart activity using multiple types of sensors to provide a more robust system that delivers safely timed pulses.

For at least the limitations described above there is a need for a multi-sensor patch and signal analyzer that enable safe cardiac ablation.

BRIEF SUMMARY OF THE INVENTION

One or more embodiments described in the specification are related to multi-sensor patch and signal analyzer that enable safe cardiac ablation. Embodiments of the invention may use redundancy of sensor data to cross-check that a heartbeat is in a safe phase to receive ablation pulses.

One or more embodiments of the invention may include a patch configured to be placed on a patient's body, and a signal analyzer coupled to the sensors and to a pulse generator that creates electrical pulses to induce cardiac ablation within the patient's body. The patch may include sensors that include one or more electrocardiogram electrodes, one or more photoplethysmogram sensors, and one or more accelerometers. It may also include one or more pulse field ablation return electrodes that are coupled electrically to the pulse generator. The signal analyzer may be configured to repeatedly obtain data from the sensors, analyze the data to identify a heartbeat and a phase of a heartbeat cycle, confirm that data from each sensor is consistent with the heartbeat and phase of the heartbeat cycle, and, when data from each of the sensors is consistent, and the phase of the heartbeat cycle is a safe time period for cardiac ablation, enable the pulse generator to generate the electrical pulses.

In one or more embodiments, the sensors on the patch may also include one or more microphones.

In one or more embodiments, the patch may include three or more electrocardiogram electrodes.

In one or more embodiments, the patch may include three or more photoplethysmogram sensors.

In one or more embodiments, the patch may include two or more pulsed field ablation return electrodes.

In one or more embodiments, the one or more pulsed field ablation return electrodes may be configured to return pulses of at least 15000 volts.

In one or more embodiments, the signal analyzer may also be configured to disable the pulse generator from generating electrical pulses when the phase of the heartbeat cycle is within a T wave.

BRIEF DESCRIPTION OF THE DRAWINGS

The above and other aspects, features and advantages of the invention will be more apparent from the following more particular description thereof, presented in conjunction with the following drawings wherein.

DETAILED DESCRIPTION OF THE INVENTION

A multi-sensor patch and signal analyzer that enable safe cardiac ablation will now be described. In the following exemplary description, numerous specific details are set forth in order to provide a more thorough understanding of embodiments of the invention. It will be apparent, however, to an artisan of ordinary skill that the present invention may be practiced without incorporating all aspects of the specific details described herein. In other instances, specific features, quantities, or measurements well known to those of ordinary skill in the art have not been described in detail so as not to obscure the invention. Readers should note that although examples of the invention are set forth herein, the claims, and the full scope of any equivalents, are what define the metes and bounds of the invention.

Intravascular catheters are used in medicine to deliver high voltage short duration pulsed electricity—also known as pulsed-field ablation (PFA), electroporation, DC ablation, fulguration—to tissue targets in a body for the purposes of soft tissue ablation. One common application is cardiac ablation, which uses electrical energy to selectively destroy small sets of cells that may be contributing to heart dysfunctions such as arrythmias. Ablation pulses should occur at specific points in the heartbeat cycle for maximum safety.

Figure 1:
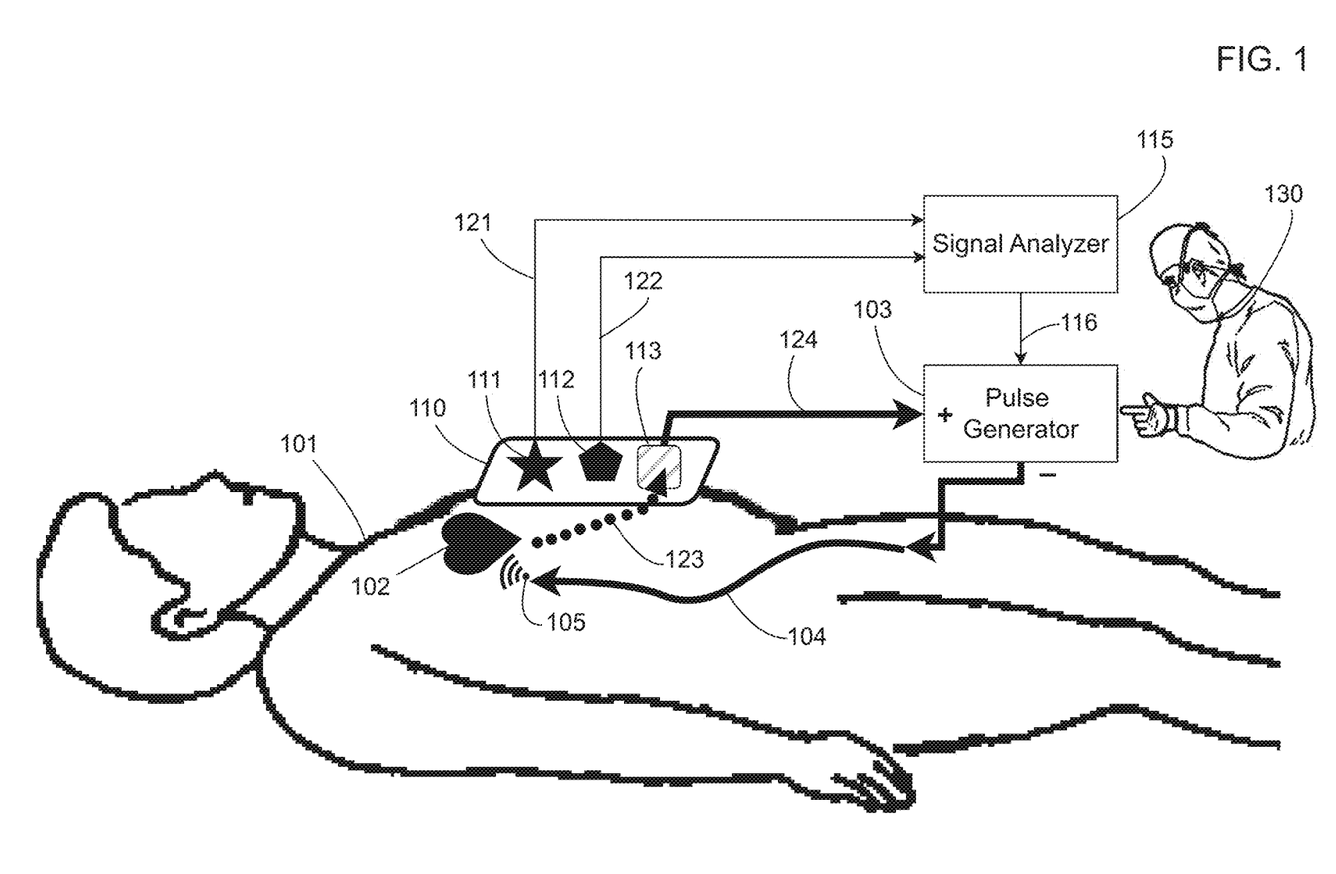
FIG. 1 shows an architectural block diagram of a system that includes a pulse generator for pulsed-field ablation, a patch attached to a patient that collects sensor data and provides an energy return path, and a signal analyzer that analyzes sensor data to determine safe time windows for PFA.

FIG. 1 shows an overview of an embodiment of the invention that uses sensors on a patch and a data analysis subsystem to control pulses, so the pulses occur at the correct time(s) in a heartbeat cycle. Patient 101 undergoes, for example, a cardiac ablation procedure for problems with the patient's heart 102. An ablation catheter is inserted into the patient's blood vessels and guided until it arrives near heart 102. There is an electrical connection 104 between a pulse generator 103 and one or more electrodes 105 on the ablation catheter. Patch 110 is attached to the patient's skin. The patch contains sensors that measure data that may be used to control the timing of ablation pulses. The patch may contain various numbers and types of sensors. Illustrative patch 110 has two sensors 111 and 112 with different modalities (for example, without limitation, sensor 111 may be an accelerometer, and sensor 112 may be an electrocardiogram (ECG) electrode). Embodiments of the invention may use any number and type or types of sensors on a patient patch; illustrative configurations are described below with respect to FIGS. 2A, 2B, and 2C. Data from sensors 111 and 112 are transmitted over connections 121 and 122 (which may be combined into a single cable), respectively, to a signal analyzer 115. This signal analyzer may for example include hardware such as a processor, a memory, and analog-to-digital converters (ADC). Signal analyzer 115 analyzes data from the patch sensors and transmits control signals 116 to pulse generator 103; these control signals may enable or disable pulse generation based on the phase of the heartbeat cycle determined from the sensor data. The pulse generator 103 may also accept input from a clinician 130, who may for example initiate or terminate a procedure, and may manually determine when to deliver pulses (within the constraints provided by the control signals 116).

In some applications the ablation catheter may be used in a unipolar mode, and patch 110 may provide a return path for current emitted from the catheter electrode. This return path feature may be provided in addition to the sensors on the patch. One or more conductive regions 113 may be included on the patch to receive current 123 that passes through the patient's body to the patch, and a return path 124 may be connected from region(s) 113 to pulse generator 103. In some embodiments, the electrical path 104 to 123 to 124 may carry pulses of very high voltage, such as 15,000 or more volts. In contrast, the sensor data paths 121 and 122 may be low voltage, such as 5 volts for example. In one or more embodiments, a power connection to power sensors 111 and 112 may also be connected from the signal analyzer (or pulse generator) to patch 110; this power supply may also be relatively low voltage such as 5 volts or 12 volts for example. In the illustrative example shown in FIG. 1, the path 104 to electrode 105 is connected to the negative pole of the pulse generator 103, and the return path 123 to 124 is connected to the positive pole of the pulse generator. In one or more embodiments these polarities may be reversed.

Illustrative types of sensors that may be included in patch 110 may include for example, without limitation, one or more ECG (electrocardiogram) electrodes, one or more accelerometers, one or more microphones, and one or more photoplethysmogram (PPG) sensors. One or more embodiments may include any subset or superset of these sensors. Use of multiple types of sensors provides redundancy to improve the reliability of detection of heartbeat phases, thereby improving patient safety. These types of sensors use different physical modalities to measure heartbeat phases: an accelerometer measures mechanical movement, a PPG is an optical sensor, an ECG detects electrical activity, and a microphone measures acoustic changes. An accelerometer tracks heartbeats through sensing mechanical movement of the chest; it may be used for example for T-wave detection. A PPG tracks heartbeats through optical sensing of changes in blood volume in the microvascular bed of chest tissue; it may be used for example for detection of P, QRS, and T waves. An ECG electrode tracks heartbeats by sensing the heart's electrical activity; it may be used for example for detection of QRS and T waves. A microphone tracks heartbeats by analyzing the heart's sound; it may be used for example for detection of QRS and T waves.

Figure 2A:
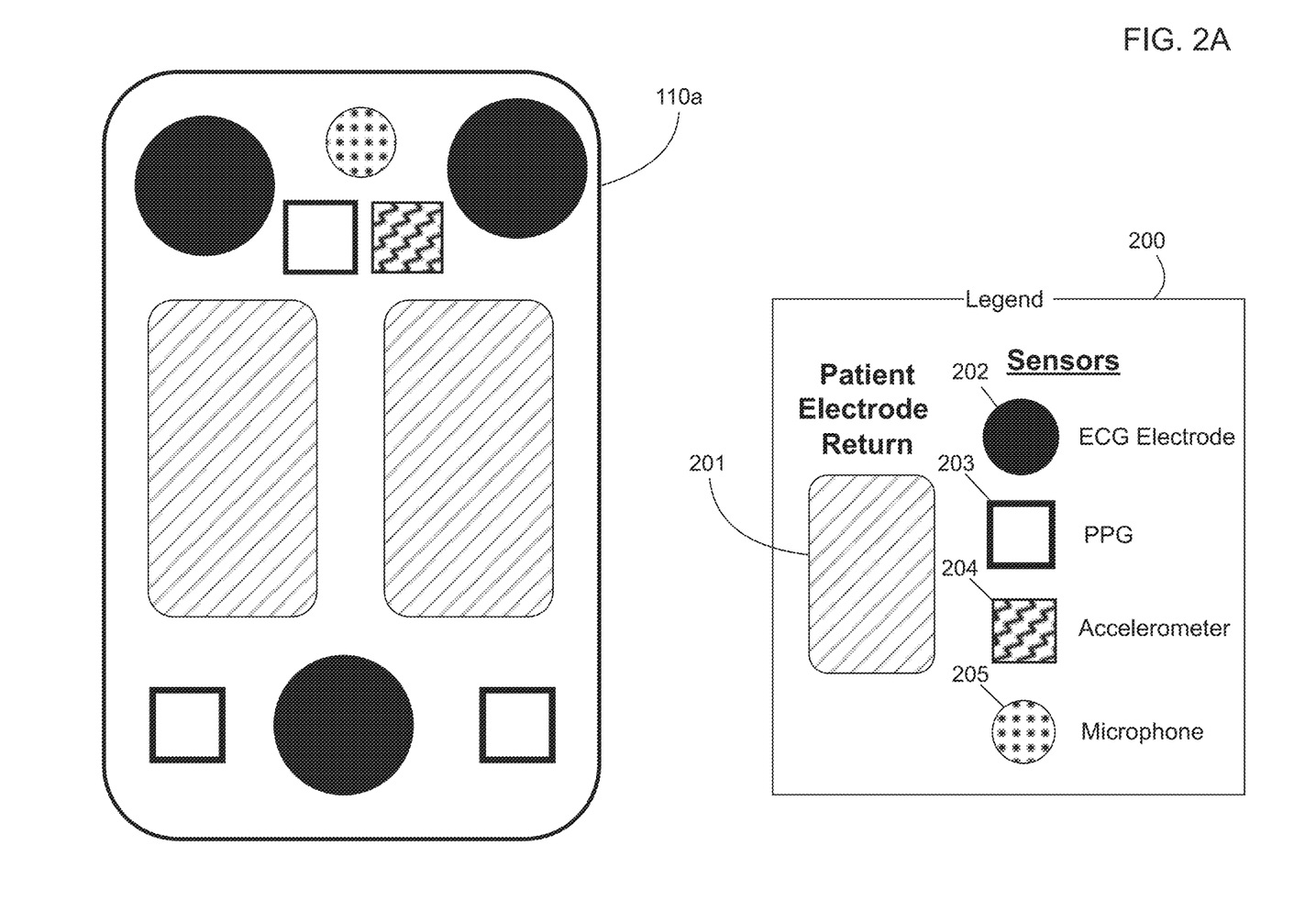
FIGS. 2A, 2B, and 2C show three illustrative configurations of a patch that collects sensor data to be used to control PFA.
Figure 2B:
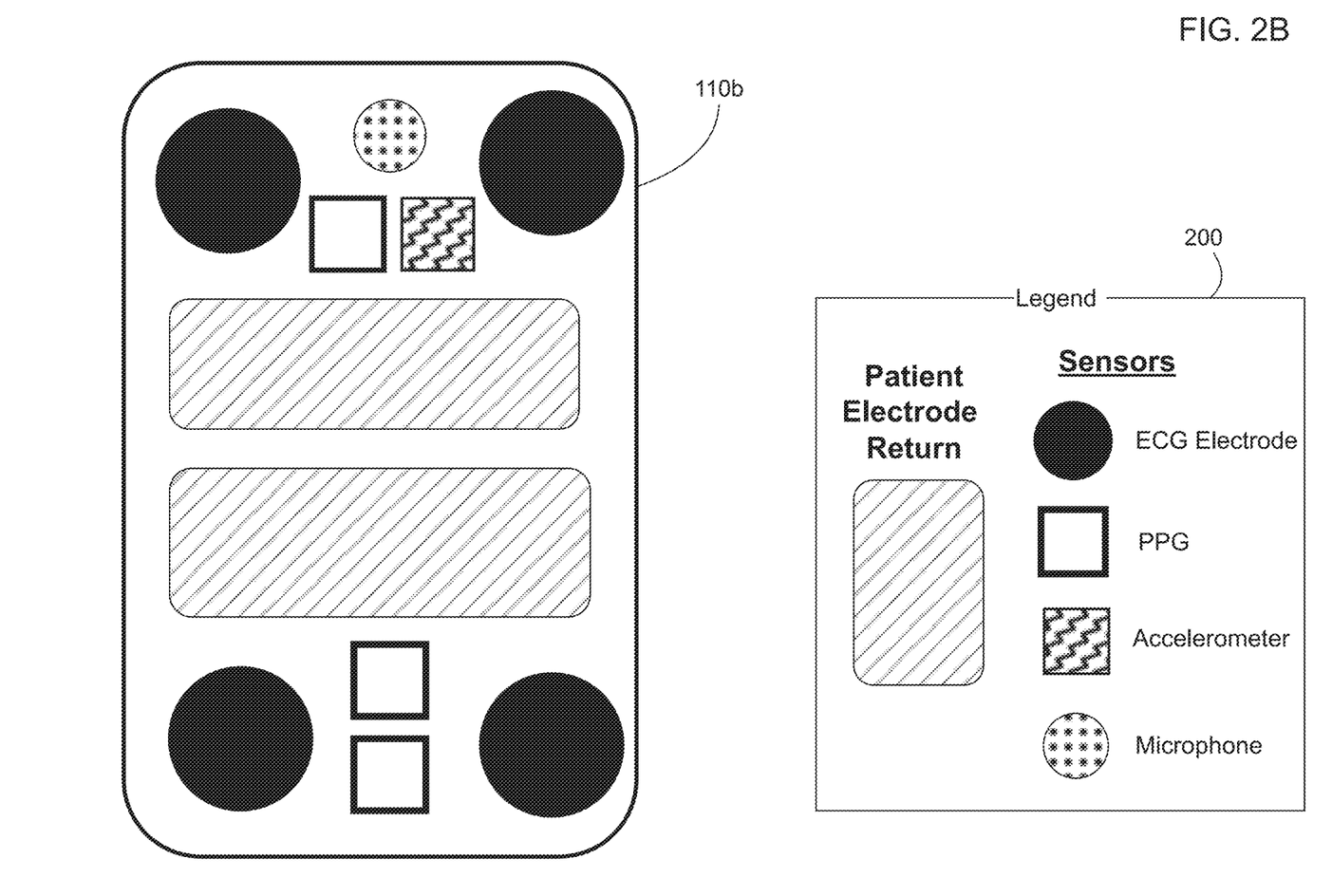
Figure 2C:
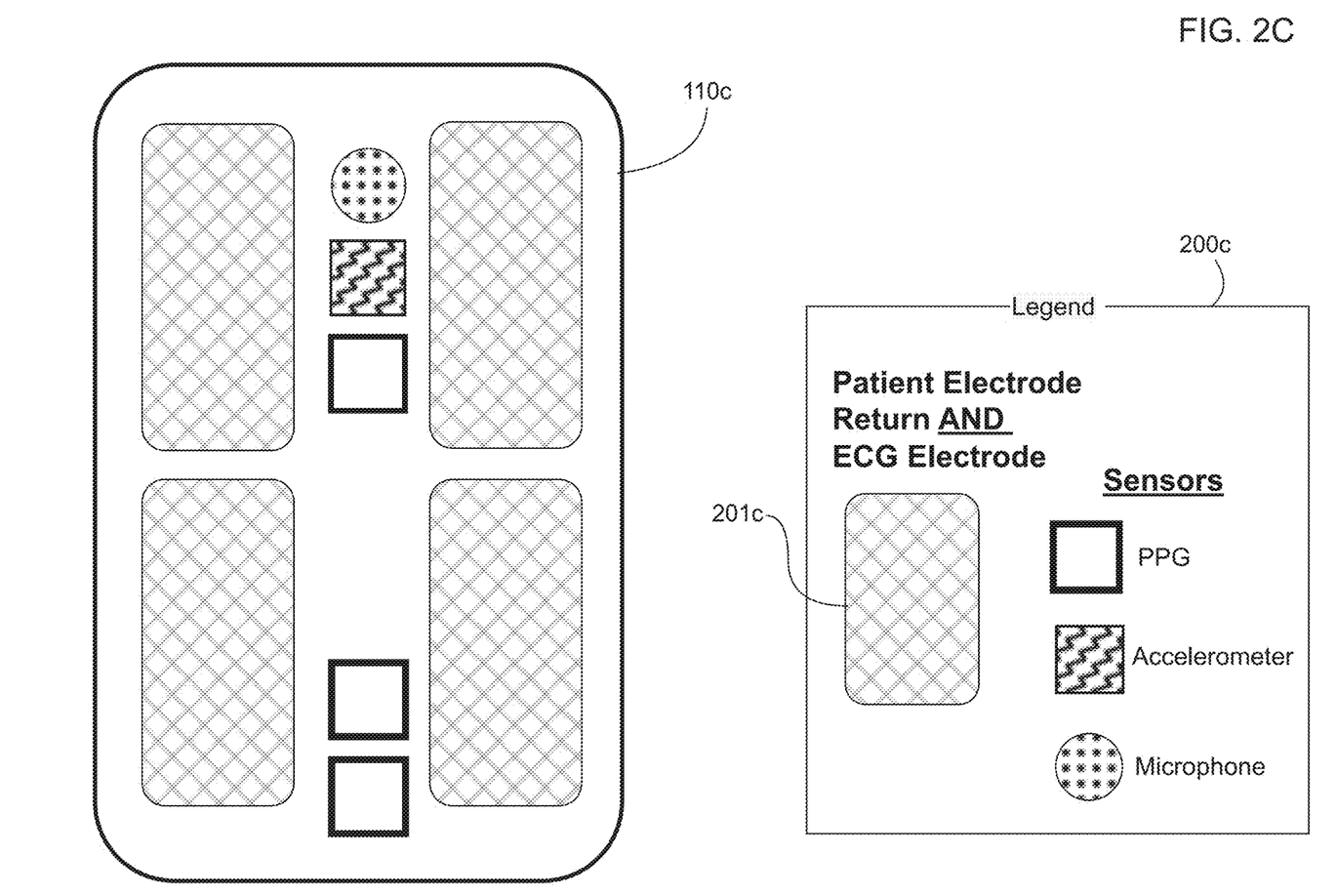

FIGS. 2A, 2B, and 2C show illustrative configurations of patient patches. Legend 200 indicates the shapes and shading that represent different types of sensors and patient electrode returns. Hatched rounded rectangles 201 indicate patient return electrodes; black circles 202 indicate ECG electrodes; white squares 203 indicate PPG sensors, zig-zagged hatched squares 204 indicate accelerometers, and dotted circles 205 indicate microphones. The physical shape and size of the sensor and return areas on a patch may not correspond directly to the figures; these areas may be of any shapes and sizes. The patch may also be of any shape and size. In one or more embodiments, multiple patches may be used with any desired configuration of sensors and return electrodes on each patch; the term "patch" in this specification may include multiple patches.

Illustrative patch 110a shown in FIG. 2A includes two patient return electrodes, three ECG electrodes, one microphone, one accelerometer, and three PPG sensors. Illustrative patch 110b shown in FIG. 2B includes two patient return electrodes, four ECG electrodes, one microphone, one accelerometer, and three PPG sensors. Illustrative patch 110c shown in FIG. 2C includes one microphone, one accelerometer, and three PPG sensors. There are four conductive regions (indicated by cross hatching 201c in legend 200c) that each serve as both return electrodes and as ECG electrodes. One benefit of combining the ECG and return electrodes is that a greater surface area can be dedicated to the return path, which may increase the safety of the PFA procedure. It may also reduce the cost and complexity of the patch.

Figure 3:
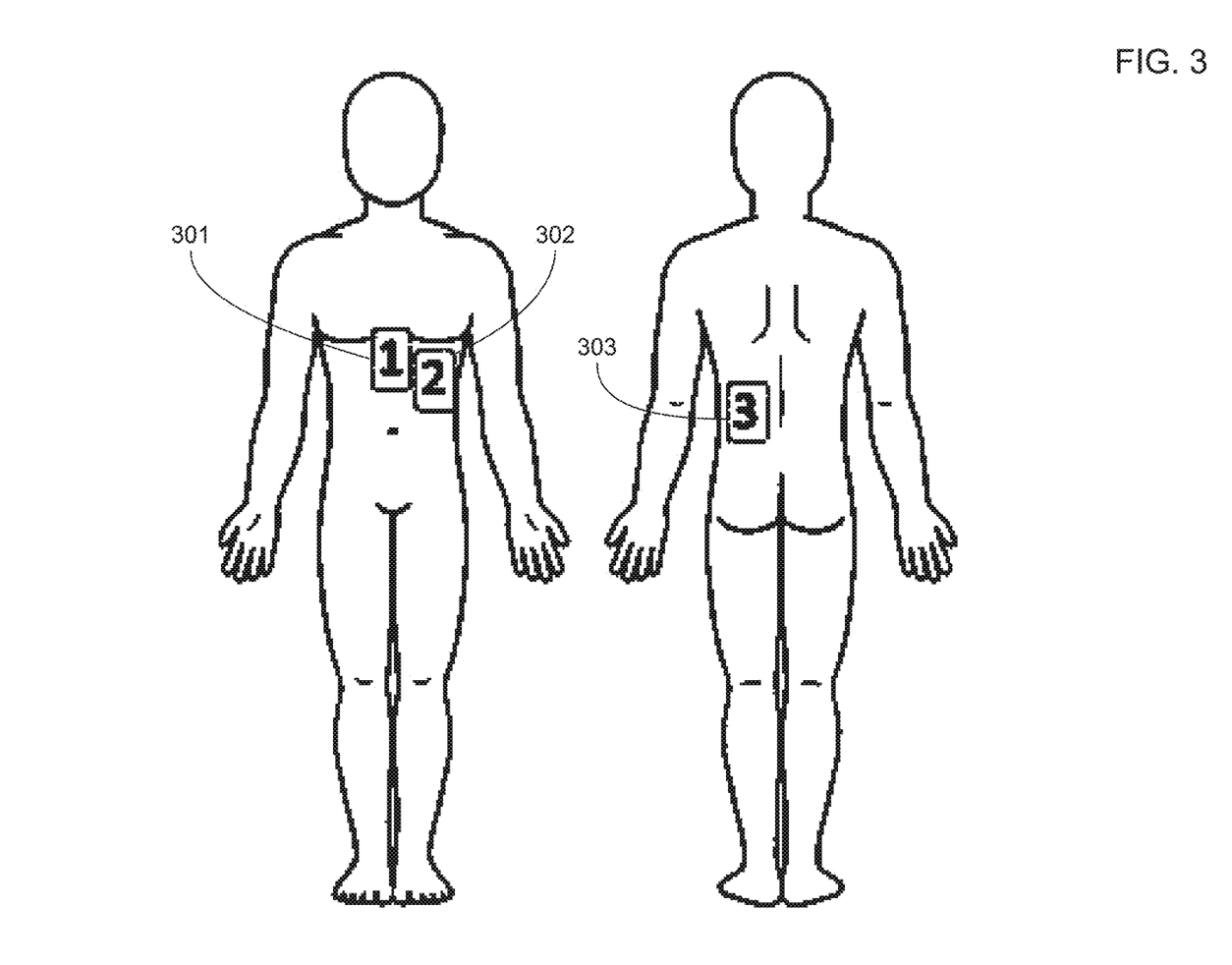
FIG. 3 shows three illustrative locations where a patch may be attached to a patient.

FIG. 3 shows three illustrative locations 301, 302, and 303 where a patch may be placed on a patient's body. In general, the patch and its included sensors and return electrodes should have good contact with the patient's skin. Accelerometers, if included, are preferably located close to the heart. If ECG electrodes are included, there should preferably be at least 3 of them, and the distance between the electrodes should be as large as possible. If PPG sensors are included, their front surface should preferably be in close contact with the skin, and the back should be shielded from ambient light. If patient return electrodes are included, they should preferentially support the voltage of the catheter electrode (such as 15 kV) and provide comparable impedance to the catheter tip to provide efficient return. The patch should preferentially be sealed for 5V (or other) power without leakage to the patient.

Figure 4:
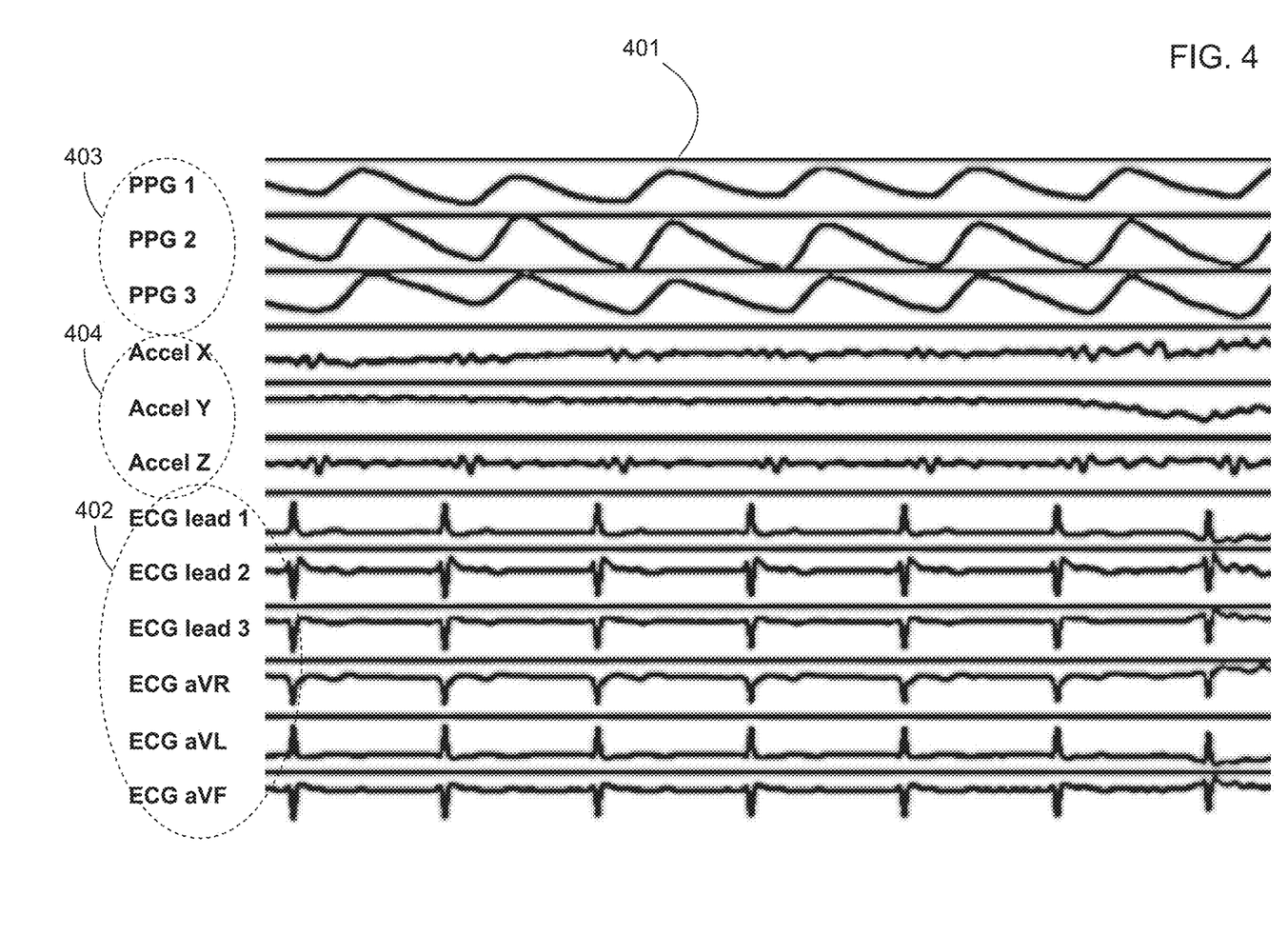
FIG. 4 shows sample waveforms collected during testing of a sensor patch, illustrating excellent correlation between data of different sensor types.

FIG. 4 shows signal waveforms 401 collected from an illustrative patch placed on a test subject; the patch includes three PPG sensors, a 3-axis accelerometer, and ECG electrodes. Data from the three PPGs 403 are consistent and highly correlated with heartbeat activity. Accelerometer data from the three accelerometer axes 404 show that the Z and X axes are highly correlated with heartbeat activity. ECG electrode data is processed to provide standard ECG lead data 402 that include leads 1, 2, 3, aVR, aVL, and aVF; these signals clearly show the main components of an ECG reading: the P wave, the QRS complex, and the T wave, which correspond to the depolarization of the atria, depolarization of the ventricles, and repolarization of the ventricles, respectively. All sensor data is highly consistent and highly correlated across sensor types, indicating that the combination of sensors provides valuable redundancy to ensure accurate detection of heartbeat phases.

Figure 5:
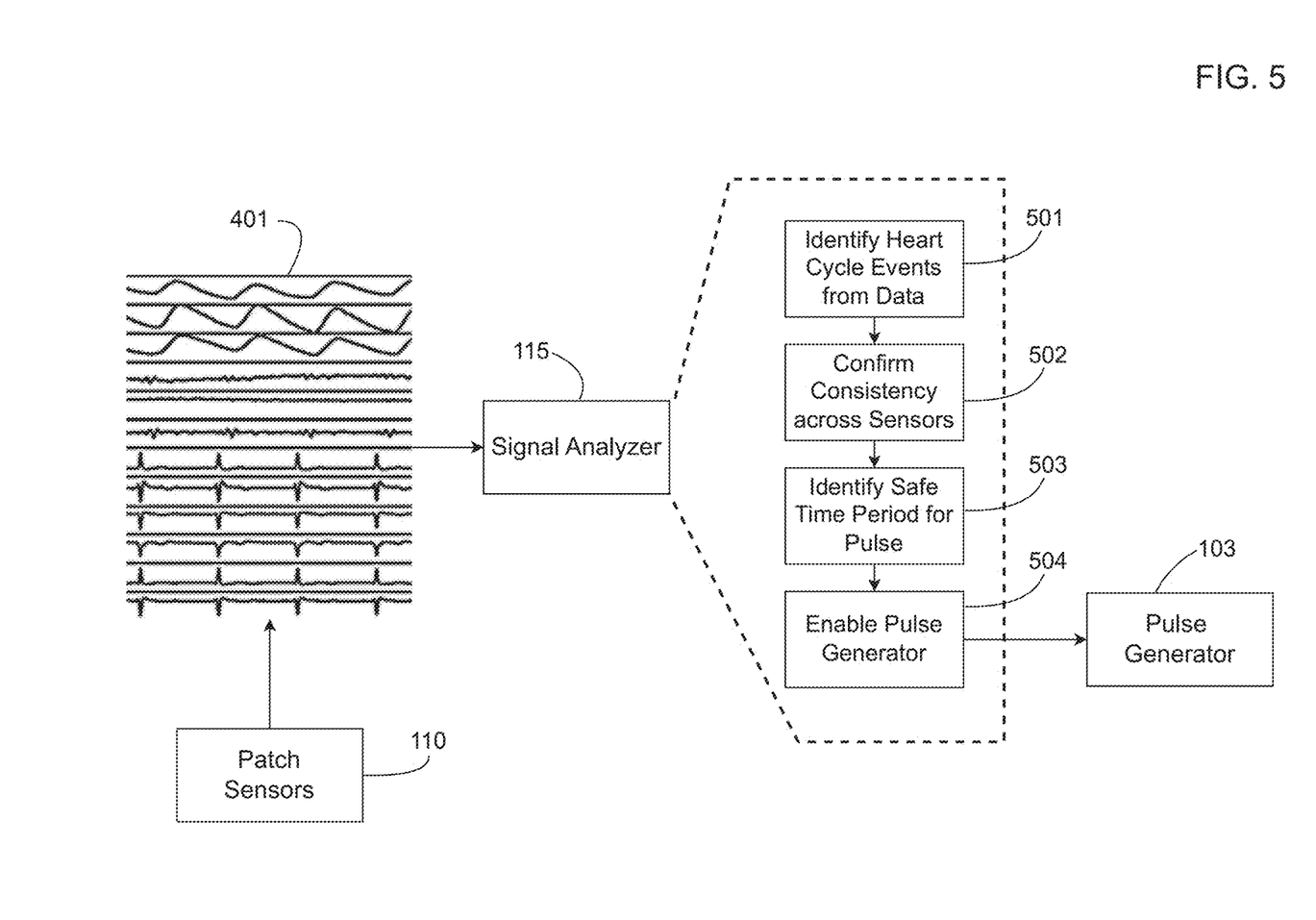
FIG. 5 shows a high-level flowchart of illustrative steps used by a signal analyzer to analyze sensor data and to control a pulse generator.

FIG. 5 shows a high-level flowchart of stages that signal analyzer 115 may perform to analyze sensor data 401 received from sensors on patch 110. In stage 501 the analyzer may identify heart cycle events from the data, and in stage 502 it may confirm consistency of this information across the different sensors on the patch. If sensor data is inconsistent, the analyzer may disable delivery of ablation pulses. If the data is consistent, stage 503 identifies a safe time period for a pulse, and then stage 504 enables the pulse generator 103 during this safe time period. In one or more embodiments, portions of the stages 501 through 504 may be performed concurrently or in different orders.

Figure 6:
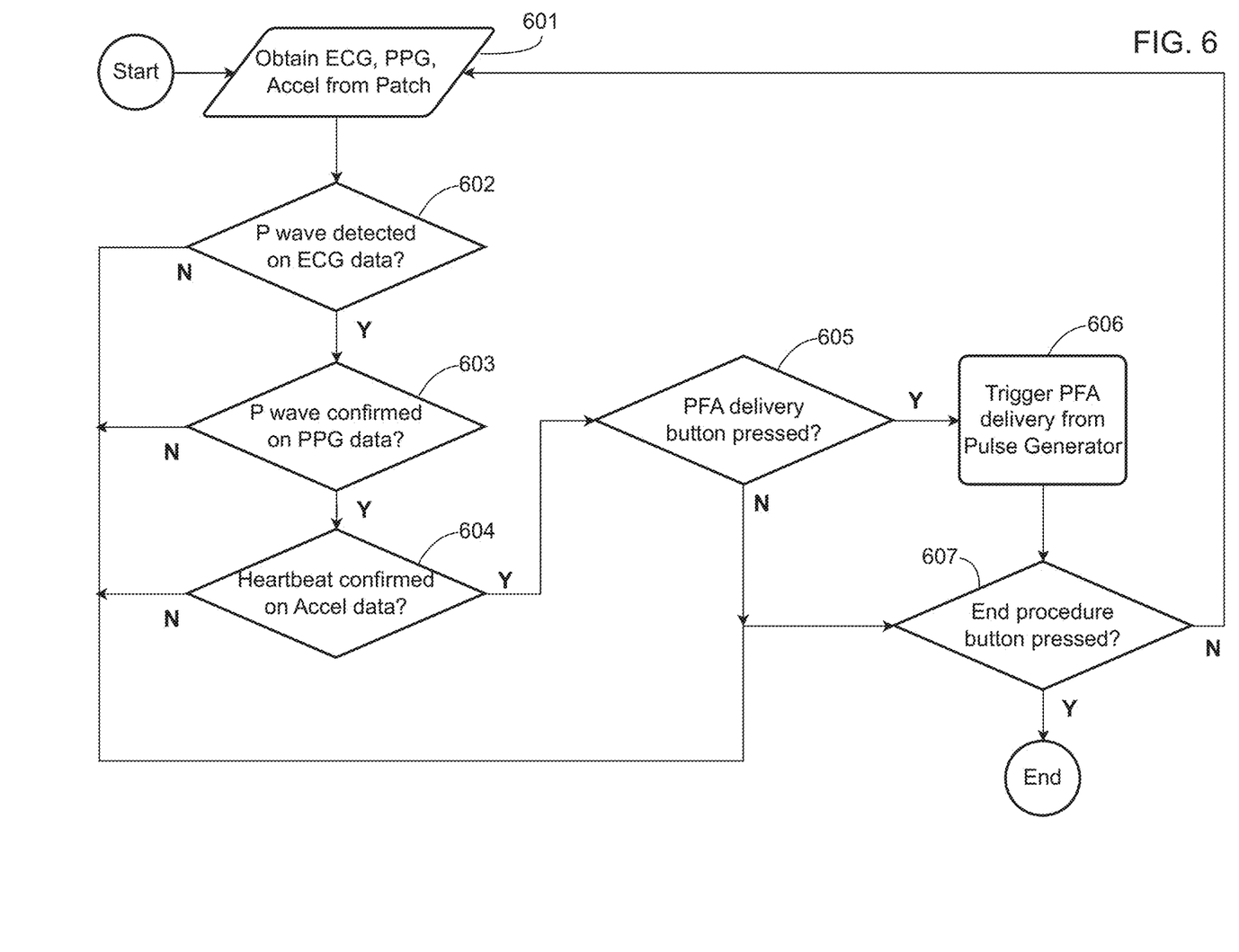
FIG. 6 shows an illustrative detailed flowchart of tests performed by a signal analyzer to determine when PFA can be applied.
Figure 7:
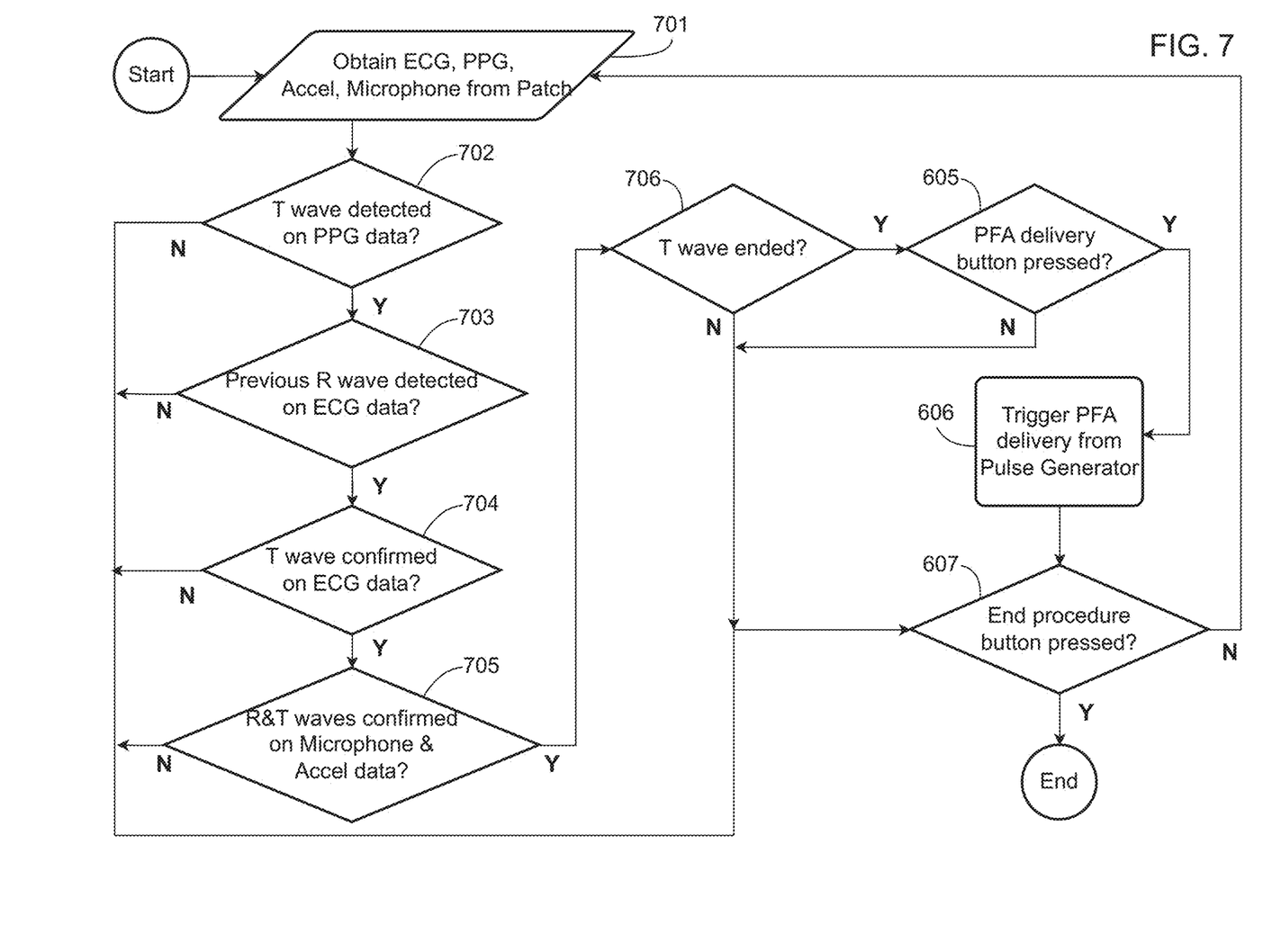
FIG. 7 shows a variation on the flowchart of FIG. 6 for a patch that includes a microphone.

FIGS. 6 and 7 show more detailed flowcharts of illustrative steps that may be performed by sensor analyzer 115. FIG. 6 shows an illustrative flowchart for analysis of data from a patch that includes one or more ECG electrodes, PPG sensors, and accelerometers. This flowchart shows a repeating loop executed at successive time periods, in which data is sampled and analyzed and pulses are either enabled or disabled at each time period. In step 601 data is obtained from the patch sensors, and then a sequence of tests 602, 603, 604 are applied to the data; if all tests succeed, and if test 605 indicates that a clinician has provided input that PFA should occur, then step 606 triggers delivery of a pulse from the pulse generator. Test 602 checks that a P wave is detected on the ECG data; test 603 cross-checks P-wave detection on PPG data; and test 604 further cross-checks that accelerometer data shows a heartbeat. At the end of the loop, a test 607 is performed to determine whether the clinician has indicated that the PFA procedure is complete; if not then the loop continues, otherwise it terminates.

FIG. 7 shows an illustrative flowchart for analysis of data from a patch that includes one or more ECG electrodes, PPG sensors, accelerometers, and microphones. As in FIG. 6, this flowchart shows a repeating loop executed at successive time periods, in which data is sampled and analyzed and pulses are either enabled or disabled at each time period. In step 701 data is obtained from the patch sensors, and then a sequence of tests 702, 703, 704, 705, and 706 are applied to the data; if all tests succeed, and if test 605 indicates that a clinician has provided input that PFA should occur, then step 606 triggers delivery of a pulse from the pulse generator. Test 702 checks whether a T wave is detected on the PPG data. If so, then tests 703 and 704 analyze ECG data to confirm detection of a T wave and to confirm detection of a previous R wave. Test 705 then confirms R wave and T wave detection on both microphone and accelerometer data. Test 706 then checks all data to confirm that the T wave has ended. If all of these tests pass, steps 605, 606, and 607 occur as described above with respect to FIG. 6.

The flowcharts shown in FIG. 6 and FIG. 7 are illustrative. One or more embodiments may use any types of analyses of sensor data to identify heart beat phases and to confirm consistency of results across sensors. The specific timing of when during the heart cycle to enable pulse generation may also vary across embodiments depending on the PFA procedure used.

While the invention herein disclosed has been described by means of specific embodiments and applications thereof, numerous modifications and variations could be made thereto by those skilled in the art without departing from the scope of the invention set forth in the claims.

What is claimed is:

1. A multi-sensor patch and signal analyzer that enable safe cardiac ablation, comprising:
   a patch configured to be placed on a patient's body, wherein said patch comprises
      a plurality of sensors that comprise
         one or more electrocardiogram electrodes;
         one or more photoplethysmogram sensors; and
         one or more accelerometers; and
      one or more pulsed field ablation return electrodes configured to be coupled electrically to a pulse generator that is configured to create electrical pulses to induce cardiac ablation within the patient's body; and
   a signal analyzer coupled to said plurality of sensors and to said pulse generator, wherein said signal analyzer is configured to repeatedly
      obtain data from each sensor of said plurality of sensors;
      analyze said data to identify a heartbeat and a phase of a heartbeat cycle;
      apply a sequence of tests to the data from said each sensor,
      confirm that data from said each sensor of all of said plurality of sensors is consistent with said heartbeat and said phase of said heartbeat cycle, from said sequence of tests applied to the data; and,
      when said sequence of tests applied to said data succeed, wherein said data from said each sensor of said plurality of sensors is consistent, and said phase of said heartbeat cycle is a safe time period for cardiac ablation, enable said pulse generator to generate said electrical pulses.

2. The multi-sensor patch and signal analyzer that enable safe cardiac ablation of claim 1, wherein said plurality of sensors further comprise one or more microphones.

3. The multi-sensor patch and signal analyzer that enable safe cardiac ablation of claim 1, wherein said one or more electrocardiogram electrodes comprise three or more electrocardiogram electrodes.

4. The multi-sensor patch and signal analyzer that enable safe cardiac ablation of claim 1, wherein said one or more photoplethysmogram sensors comprise three or more photoplethysmogram sensors.

5. The multi-sensor patch and signal analyzer that enable safe cardiac ablation of claim 1, wherein said one or more pulsed field ablation return electrodes comprise two or more pulsed field ablation return electrodes.

6. The multi-sensor patch and signal analyzer that enable safe cardiac ablation of claim 1, wherein said one or more pulsed field ablation return electrodes are configured to return pulses of at least 15000 volts.

7. The multi-sensor patch and signal analyzer that enable safe cardiac ablation of claim 1, wherein said signal analyzer is further configured to, when said phase of said heartbeat cycle is within a T wave, disable said pulse generator from generating said electrical pulses.

8. The multi-sensor patch and signal analyzer that enable safe cardiac ablation of claim 1, wherein said sequence of tests comprise a first test to check whether a T wave is detected on said data from said one or more photoplethysmogram sensors.

9. The multi-sensor patch and signal analyzer that enable safe cardiac ablation of claim 8, wherein said sequence of tests further comprises a second test and a third test, wherein if said T wave is detected via said first test, said second test and said third test analyze said data from said one or more electrocardiogram electrodes to confirm detection of said T wave and to confirm detection of a previous R wave.

10. The multi-sensor patch and signal analyzer that enable safe cardiac ablation of claim 9, wherein said plurality of sensors further comprise one or more microphones, and wherein said sequence of tests further comprises a fourth test to confirm R wave and T wave detection on said data from said one or more microphones and from said one or more accelerometers.

11. The multi-sensor patch and signal analyzer that enable safe cardiac ablation of claim 10, wherein said sequence of tests further comprises a fifth test that check said data from all of said plurality of sensors to confirm that said T wave has ended.

12. The multi-sensor patch and signal analyzer that enable safe cardiac ablation of claim 1, wherein said analyze said data to identify a heartbeat and a phase of a heartbeat cycle comprises analyzing said data from said sensor to determine safe time windows to deliver said cardiac ablation, wherein heart cycle events are identified in said data.

13. A multi-sensor patch and signal analyzer that enable safe cardiac ablation, comprising:
 a patch configured to be placed on a patient's body, wherein said patch comprises
  a plurality of sensors that comprise
   one or more electrocardiogram electrodes;
   one or more photoplethysmogram sensors; and
   one or more accelerometers; and
   one or more pulsed field ablation return electrodes configured to be coupled electrically to a pulse generator that that is configured to create electrical pulses to induce cardiac ablation within the patient's body; and
 a signal analyzer coupled to said plurality of sensors and to said pulse generator, wherein said signal analyzer is configured to repeatedly
  obtain data from each sensor of said plurality of sensors;
  analyze said data to identify a heartbeat and a phase of a heartbeat cycle;
  apply a sequence of tests to the data from said each sensor,
  confirm that data from said each sensor of all of said plurality of sensors is consistent with said heartbeat and said phase of said heartbeat cycle, from said sequence of tests applied to the data; and,
  when said sequence of tests applied to said data succeed, wherein said data from said each sensor of said plurality of sensors is consistent, and said phase of said heartbeat cycle is a safe time period for cardiac ablation, enable said pulse generator to generate said electrical pulses;
 wherein said sequence of tests comprise a first test to check whether a T wave is detected on said data from said one or more photoplethysmogram sensors;
 wherein said sequence of tests further comprises a second test and a third test, wherein if said T wave is detected via said first test, said second test and said third test analyze said data from said one or more electrocardiogram electrodes to confirm detection of said T wave and to confirm detection of a previous R wave;
 wherein said plurality of sensors further comprise one or more microphones, and wherein said sequence of tests further comprises a fourth test to confirm R wave and T wave detection on said data from said one or more microphones and from said one or more accelerometers;
 wherein said sequence of tests further comprises a fifth test that check said data from all of said plurality of sensors to confirm that said T wave has ended; and
 wherein said analyze said data to identify a heartbeat and a phase of a heartbeat cycle comprises analyzing said data from said sensor to determine safe time windows to deliver said cardiac ablation, wherein heart cycle events are identified in said data.

* * * * *